United States Patent
Chen

(10) Patent No.: US 8,398,838 B2
(45) Date of Patent: Mar. 19, 2013

(54) TECHNICAL MEASURE FOR GEL ELECTROPHORESIS SHAPING

(75) Inventor: Hui-Wan Chen, Taipei County (TW)

(73) Assignee: Wealtec Bioscience Co., Ltd., New Taipei (TW)

( * ) Notice: Subject to any disclaimer, the term of this patent is extended or adjusted under 35 U.S.C. 154(b) by 1164 days.

(21) Appl. No.: 12/285,642

(22) Filed: Oct. 10, 2008

(65) Prior Publication Data

US 2010/0089755 A1    Apr. 15, 2010

(51) Int. Cl.
*B29C 35/02* (2006.01)
(52) U.S. Cl. ........ 204/470; 204/450; 204/469; 204/466; 204/467
(58) Field of Classification Search .......... 204/450–470, 204/600–621
See application file for complete search history.

(56) References Cited

U.S. PATENT DOCUMENTS

| 3,595,531 | A | * | 7/1971 | Williams et al. | 366/273 |
| 3,924,836 | A | * | 12/1975 | Bruning et al. | 366/76.6 |
| 4,966,792 | A | * | 10/1990 | Terai et al. | 427/358 |

FOREIGN PATENT DOCUMENTS

JP         01127946 A   *  5/1989

* cited by examiner

*Primary Examiner* — Keith Hendricks
*Assistant Examiner* — Bach Dinh

(57) ABSTRACT

A technical measure for gel electrophoresis shaping that can make the gel electrophoresis generate no bubbles including in the gel, and can make a gradient gel being more accurate and more stable in quality. When liquid gel enters a collecting trough under continuous driving of a roller in the collecting trough to be injected into a carrier sheet set from a gel output port and a narrow seam, former injected liquid gel can be pushed upwards by latter injected liquid gel, and an accomplished product of gel can be obtained. If the collecting trough is input with two liquid basic materials, the liquid gel continuously output into the carrier sheet set can have a gradient.

6 Claims, 9 Drawing Sheets

TECHNICAL MEASURE FOR GEL ELECTROPHORESIS SHAPING

BACKGROUND OF THE INVENTION

1. Field of the Invention

The invention relates to a technical measure for gel electrophoresis shaping, and especially to a method of gel electrophoresis shaping and a shaping device for the method to be suitable for being used to make a gradient gel.

2. Description of the Prior Art

An electrophoresis device is a device widely used in the fields of molecular biology, genetics and biochemistry, while gel electrophoresis normally will encounter the problems of generation of bubbles and hardness of controlling gradient in manufacturing.

As shown in FIG. 1 which shows a schematic view of the conventional mode of gel electrophoresis shaping, wherein an earlier gel electrophoresis manufacturing method forms between two glass sheets of a carrier sheet set 90 a thin sheet receiving space 91 for injecting therein liquid gel that is cured and shaped thereafter, in the mode of injecting of the liquid gel, the liquid gel drips in the thin sheet receiving space 91 from a top opening 92 of the latter with a dripping pipe 100, the liquid gel flows to the bottom from the top of the thin sheet receiving space 91; when the level of the injected liquid gel rises to a predetermined height, the liquid gel is laid for a period of time to be cured, and then an accomplished gel product can be obtained; however, such a method of injecting the liquid gel dripping with the dripping pipe is much subjected to inducing the problem of generating bubbles including in the gel; and more, in manufacturing gradient gel, the mode of manual operation must be adopted to drip the liquid gel in with gradient difference layer by layer, this is quite consumptive of hours and effort.

As shown in FIG. 2 which shows another schematic view of the conventional mode of gel electrophoresis shaping, in order to eliminate the problem of generating bubbles including in the gel, another method for gel electrophoresis manufacturing provides by insertion on the bottom of the thin sheet receiving space 91 a plurality of gel injecting pipes 200, the end openings of these gel injecting pipes 200 are at the bottom of the thin sheet receiving space 91, so that the injected liquid gel is pushed and dispersed gradually upwards and to the two lateral sides taking the end openings of these gel injecting pipes 200 as a center; although such injection method with a plurality of gel injecting pipes 200 inserted on the bottom of the thin sheet receiving space 91 can solve the problem of generating bubbles in the above mentioned measure of dripping with the dripping pipe, when in performing manufacturing of gradient gel, by virtue that the liquid gel will be pushed and dispersed gradually upwards and to the two lateral sides taking the end openings of these gel injecting pipes 200 as a center and will be raised to form an arched shape, the density in an identical level of the gradient gel will gradually change and will be less accurate, and this may create a state of presenting different densities or ratios of mixing of the gel in an identical level.

In view of this, the inventor of the present invention studied and improved the gel electrophoresis shaping technique, and further solved the problem of generating bubbles including in the gel and the problem of gradually becoming inaccuracy of density in an identical level of the gradient gel.

SUMMARY OF THE INVENTION

The primary object of the present invention is to provide a method of gel electrophoresis shaping and a shaping device that can make gel electrophoresis generate no bubbles including in the gel, and can make the density in an identical level of the gradient gel change gradually to be more accurate.

To obtain the above object, the method of gel electrophoresis shaping of the present invention stands a carrier sheet set on a seat; the carrier sheet set has a thin sheet receiving space for injecting therein liquid gel that is cured and shaped thereafter, and the carrier sheet set is provided on its bottom an elongate narrow seam in communication with the thin sheet receiving space, the seat is provided with an elongate gel output port at a position in corresponding to that of and with a width coincident with that of the narrow seam and with an opening facing upwards, when the gel enters the thin sheet receiving space via the bottom continuously from the gel output port and the narrow seam under continuous driving of a roller of a collecting trough, the former injected liquid gel can be pushed upwards by the latter injected liquid gel and is gradually injected into the thin sheet receiving space, and after being cured of the liquid gel, an accomplished product of gel can be obtained.

When in practicing, the liquid gel can be composed of two liquid basic materials, and the seat is provided at the upstream end of the gel output port with a cylindrical collecting trough for collecting the two liquid basic materials, the collecting trough is provided therein with a roller with a diameter slightly smaller than that of the collecting trough itself, so that when the roller rotates continuously, the two liquid basic materials flowing in are continuously output to the gel output port; the width of the collecting trough is coincident with that of the gel output port, so that the gel output port can make evenly outputting of the liquid gel to every area of the narrow seam.

The amount of supplying for the two liquid basic materials is controlled respectively by two wriggling pumps which are actuated to control supply of the two liquid basic materials; thereby by driving of continuously rotating of the roller in the collecting trough, the liquid gel continuously output into the carrier sheet set has a gradient. The method of forming the gradient is as follows:

When the first kind of the liquid basic materials is continuously input to the collecting trough, and then the second kind liquid basic material is input to the collecting trough, by continuously rotating of the roller, the two liquid basic materials input to the collecting trough are output directly, thus the second kind liquid basic material enters the first kind liquid basic material in a mode of gradually increasing mixing ratio, thereby the continuously output liquid gel can form a gradient by the fact that the mixing ratio of the second kind liquid basic material is gradually increased.

In practicing, the above two liquid basic materials are separately injected into two receiving troughs at the upstream of the collecting trough, and each receiving trough is provided on its bottom with an elongate flow leading channel with a width coincident with that of the collecting trough which makes each liquid basic material not be concentrated at any area but evenly dispersed during continuously inputting of the basic material to the collecting trough, thereby the gradient of the liquid gel is more accurate; wherein one of the flow leading channel is provided therein with a check valve to prevent back flowing of the corresponding liquid basic material.

The shaping device for gel electrophoresis of the present invention at least comprises:

a seat having an elongate gel output port with an opening facing upwards;

a positioning member provided on the upper periphery of the gel output port; and a carrier sheet set mounted vertically on the positioning member, the carrier sheet set has a thin sheet receiving space of which the bottom is provided with an elongate narrow seam, the width of the gel output port is in coincident with that of the narrow seam and is located below the latter.

The liquid gel is composed of two basic materials, and the seat is provided at the upstream end of the gel output port with a cylindrical collecting trough of which the width coincident with that of the gel output port; the collecting trough is provided therein with a roller with a diameter slightly smaller than that of the collecting trough, the collecting trough is provided at the upstream thereof with two receiving troughs for injecting therein the two liquid basic materials into a corresponding receiving trough of them, the receiving trough is provided on its bottom with an elongate flow leading channel with a width coincident with that of the collecting trough, each receiving trough is connected at its upstream side with a wriggling pump to control supply of one of the two liquid basic materials; and at least one of the flow leading channels is provided therein with a check valve.

The carrier sheet set includes a front carrier sheet, a rear carrier sheet and two spacing sheets between the front and the rear carrier sheets, so that the two carrier sheets form therebetween the above mentioned thin sheet receiving space.

The positioning member includes a positioning frame fixed on the seat, and two lateral pressing plates pivotally provided at two lateral sides of and in front of the positioning frame; the positioning frame is provided in front of it with a positioning trough for placing the carrier sheet set; the positioning trough is provided on its bottom with an elongate hole in connection with the gel output port; the positioning trough further is provided on two lateral sides of its front wall with two upright height adjusting grooves each with a height control plate therein, the wall of the height adjusting groove is provided thereon with an upper and a lower recess, and the height control plate has positioning protrusions in cooperation with the upper and the lower recesses; the height control plate has thereon two protruding pieces respectively provided on the top and the bottom of the rear carrier sheet, and the positioning trough further is provided in front of it and on its top with two pressing cams in contact with an upper edge of the rear carrier sheet.

The gel output port of the seat is provided on its periphery with a connecting groove for longitudinally placing therein the positioning member, and the positioning member is provided on its lateral sides with two transverse positioning grooves, the seat is provided with two positioning handles each being cooperating with a transverse positioning groove, each positioning handle has on its end an engaging plate that can be pivoted transversely to enter one of the transverse positioning grooves.

As compared with the prior art, the present invention uses the wriggling pump to control supply of the two liquid basic materials, and by rotating of the roller continuously, the two liquid basic materials flowing in are continuously output, so that when the level of the injected liquid gel rises, the density of the liquid gel increases, hence the gel electrophoresis is formed with a gradient of which the density is gradually increased downwardly from above; besides, in the present invention, the liquid gel will be pushed gradually and upwardly from below with its surface kept horizontal, and this may render the gel in an identical level to have same density and mixing ratio. Thus gradient gel being more accurate and more stable in quality can be produced, and there will no bubble generated in the process of production.

The present invention will be apparent according to its technical measure and its mode of practicing after reading the detailed description of the preferred embodiment thereof in reference to the accompanying drawings.

DETAILED DESCRIPTION OF THE PREFERRED EMBODIMENT

Figure 1:
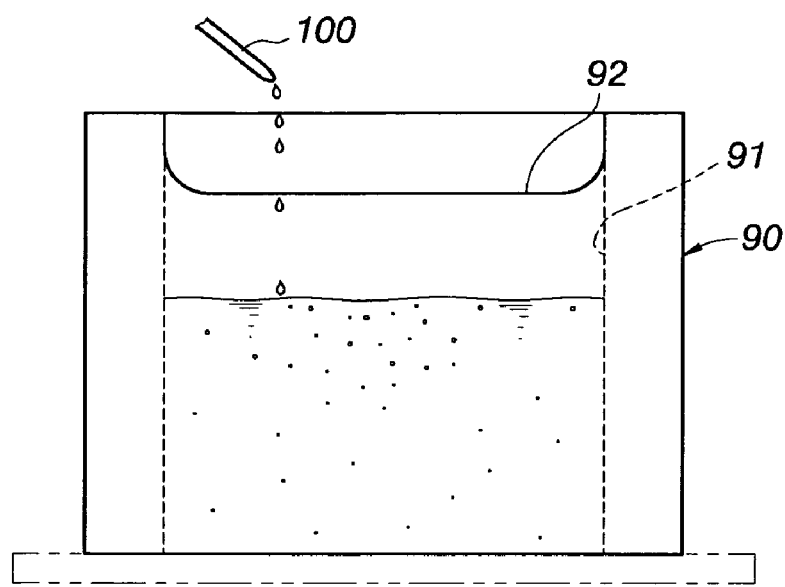
FIG. 1 is a schematic view showing a conventional mode of gel electrophoresis shaping.
Figure 2:
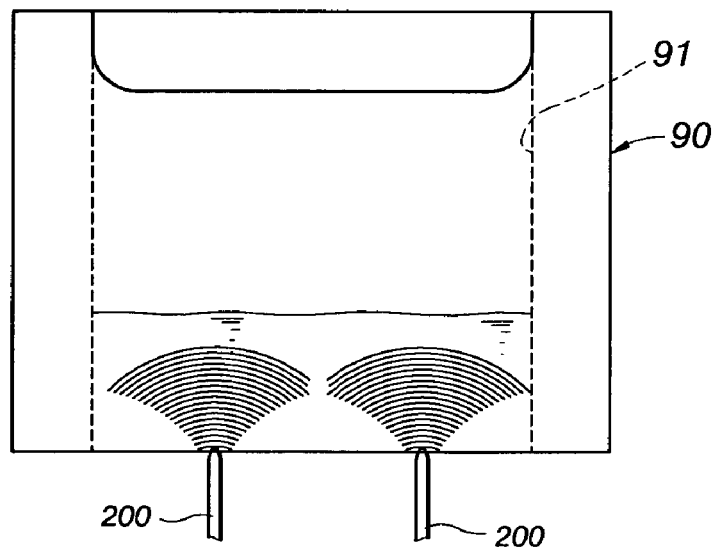
FIG. 2 is a schematic view showing another conventional mode of gel electrophoresis shaping.
Figure 3:
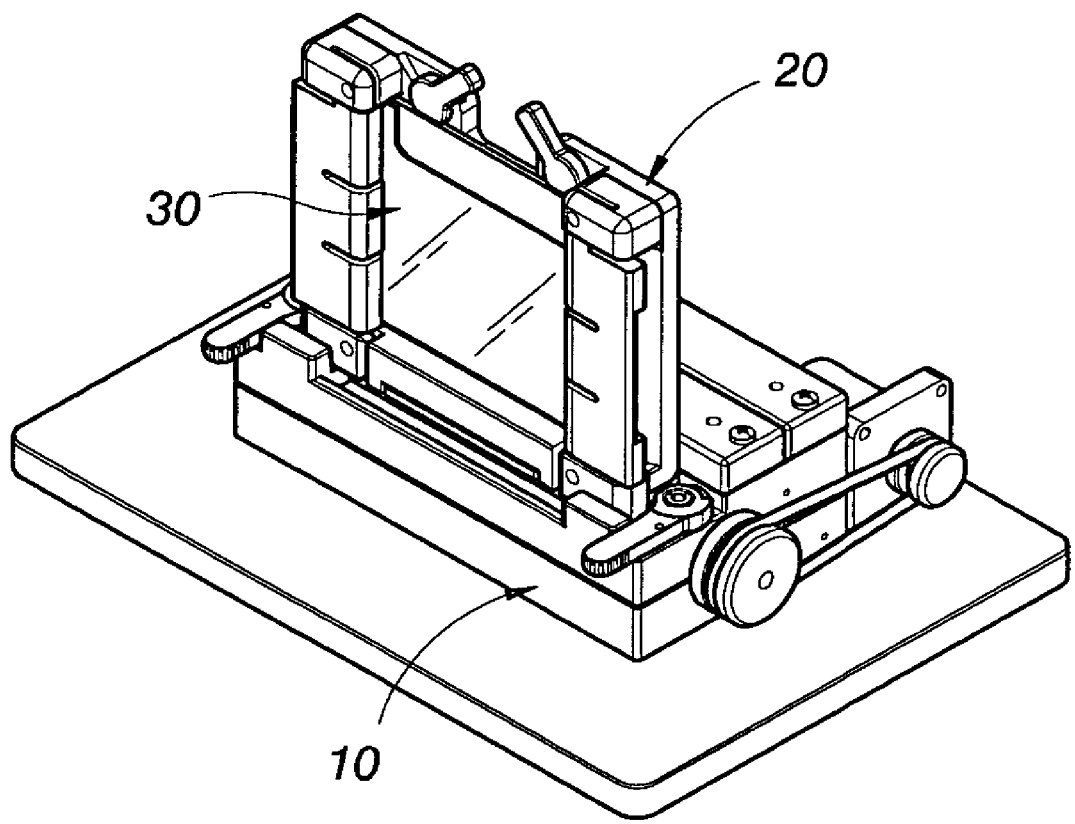
FIG. 3 is a perspective view showing a most preferred embodiment of a device of the present invention.
Figure 4:
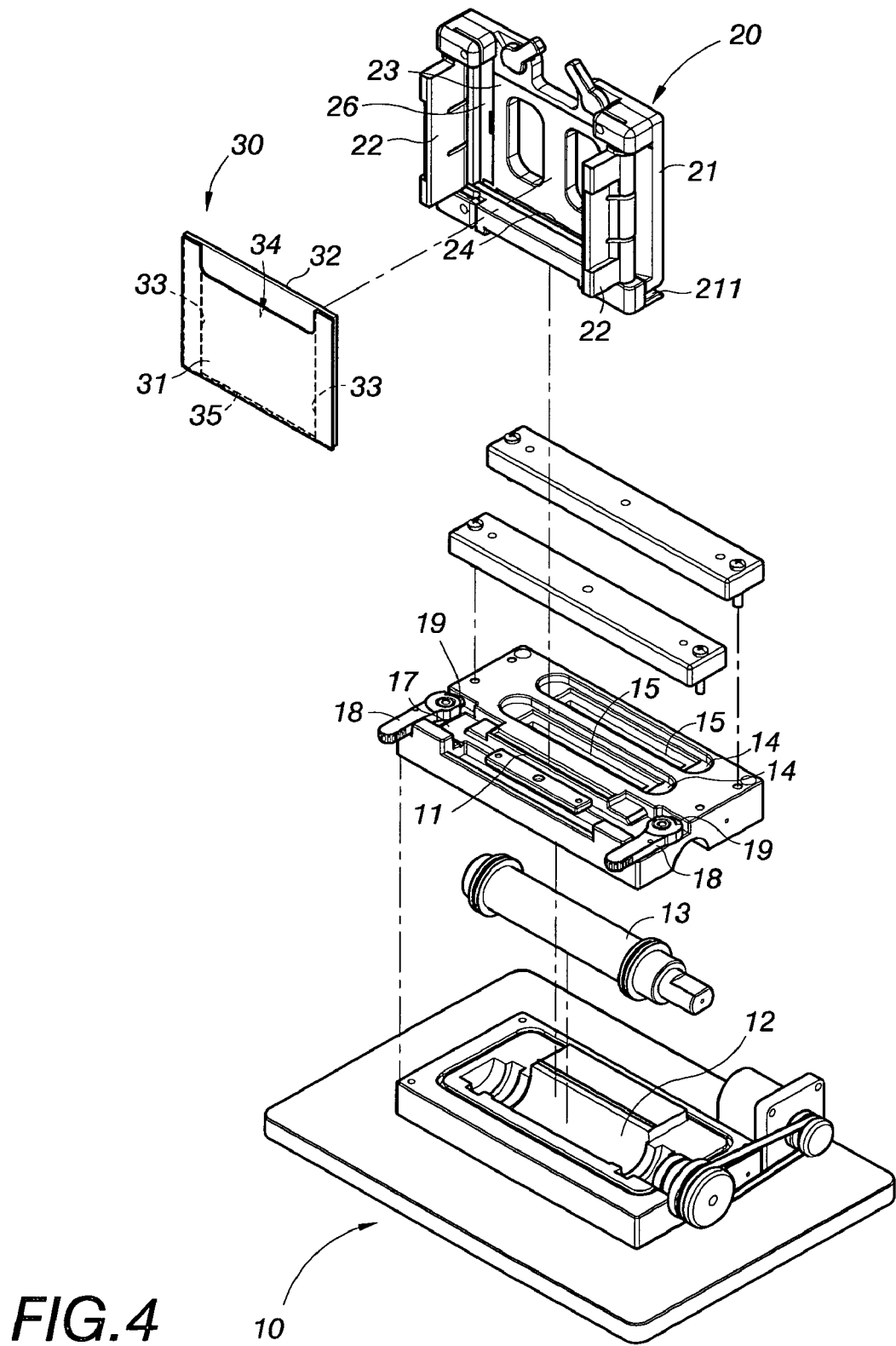
FIG. 4 is an anatomic perspective view showing the most preferred embodiment of the device of the present invention.

As shown in FIGS. 3 and 4 which are perspective views showing a most preferred embodiment of a gel electrophoresis shaping device of the present invention, wherein the gel electrophoresis shaping device comprises a seat 10, a positioning member 20 and a carrier sheet set 30; the positioning member 20 is used to bear the carrier sheet set 30, and can be fixed on the seat 10 which is used to input liquid gel into the carrier sheet set 30, an accomplished gel can be formed after curing.

Figure 5:
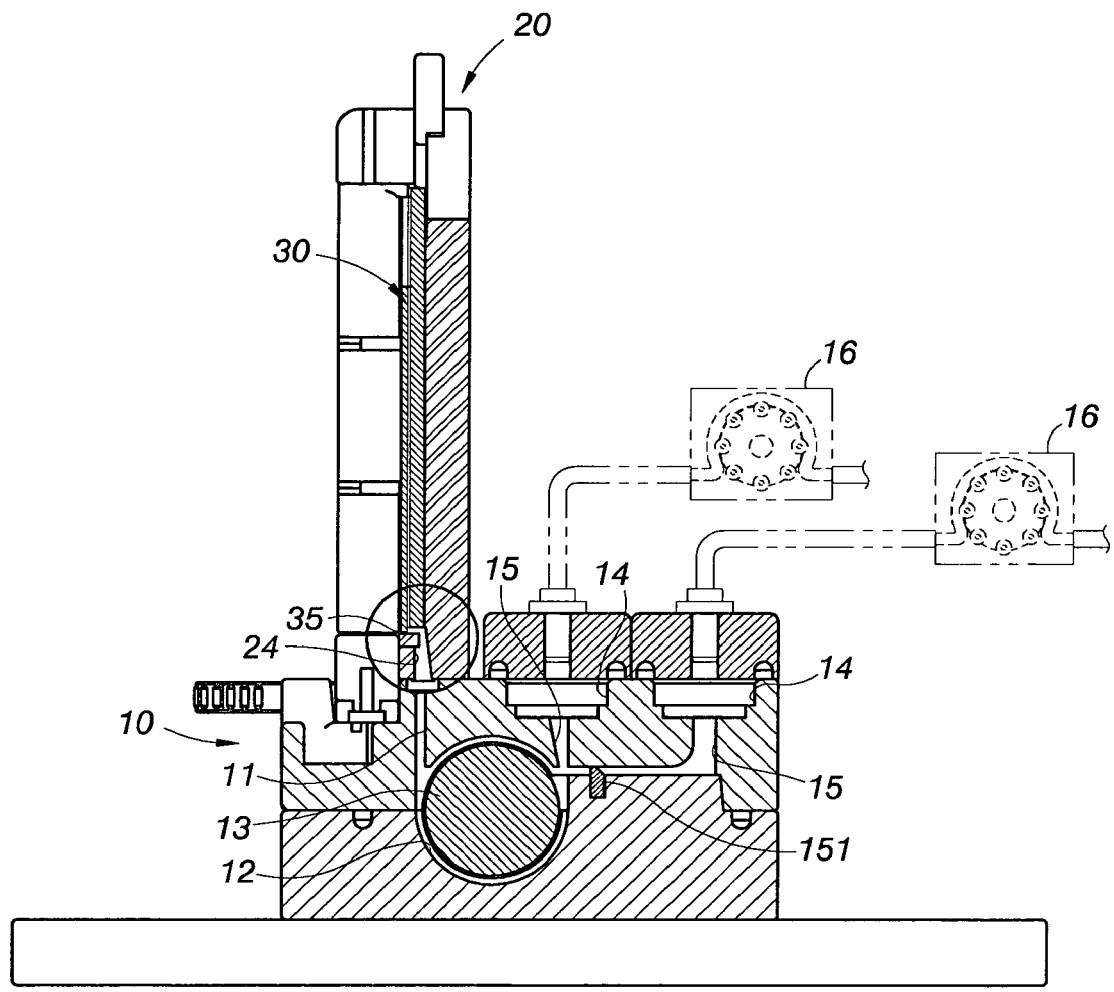
FIG. 5 is a sectional view of the most preferred embodiment of the device of the present invention.

Referring to FIGS. 4 and 5, the seat 10 has an elongate gel output port 11 with an opening facing upwards; the seat 10 is provided at an upstream end of the gel output port 11 with a cylindrical collecting trough 12, the width of the collecting trough 12 is coincident with that of the gel output port 11, the collecting trough 12 is provided therein with a roller 13 with a diameter slightly smaller than that of the collecting trough 12 itself, two receiving troughs 14 are provided at the upstream of the collecting trough 12 for injecting therein two different liquid basic materials, and each receiving trough 14 is provided on its bottom with an elongate flow leading channel 15 with a width coincident with that of the collecting trough 12, each receiving trough 14 is connected at its upstream side with a wriggling pump 16 to control supply of the two liquid basic materials; and at least one of the flow leading channels 15 is provided therein with a check valve 151; the gel output port 11 of the seat 10 is provided on its periphery with a connecting groove 17 for longitudinally placing therein the positioning member 20.

Figure 7:
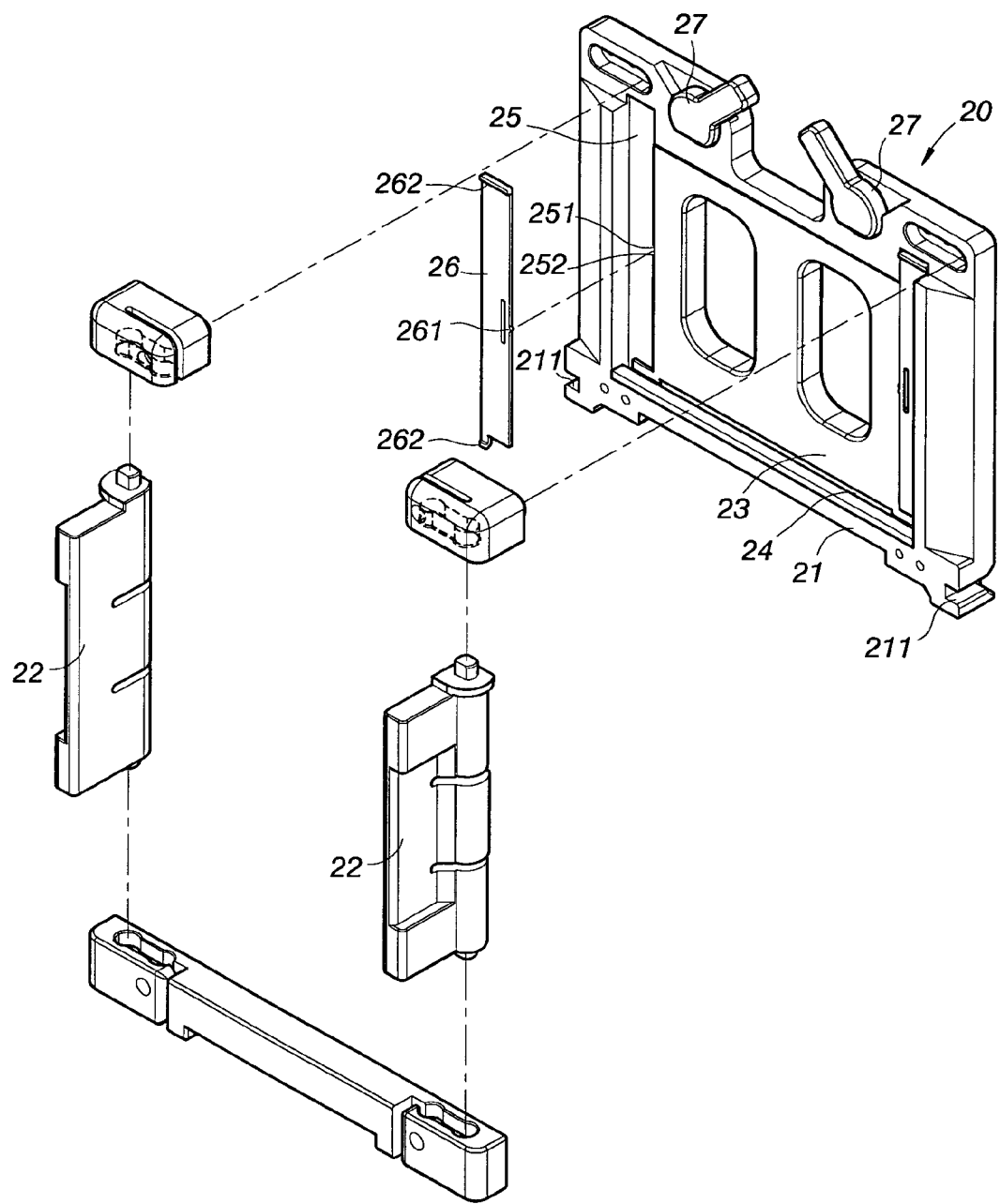
FIG. 7 is an anatomic perspective view showing a positioning member of the device of the most preferred embodiment of the present invention.

Referring to FIGS. 4 and 7, the latter is an anatomic perspective view showing the positioning member 20 of the device of the present invention, the positioning member 20 includes a positioning frame 21 for longitudinally placing therein the positioning member 20, and two lateral pressing plates 22 are pivotally provided at two lateral sides of and in front of the positioning frame 21.

The positioning frame 21 is provided at its lateral sides with two transverse positioning grooves 211, the seat 10 is provided with two positioning handles 18 each being cooperating with a transverse positioning groove 211, each positioning handle 18 has on its end an engaging plate 19 that can be pivoted transversely to enter one of the transverse positioning grooves 211.

The positioning frame 21 is provided in front of it with a positioning trough 23 for placing the carrier sheet set 30; the positioning trough 23 is provided on its bottom with an elongate hole 24 in connection with the gel output port 11; the positioning trough 23 further is provided on two lateral sides of its front wall with two upright height adjusting grooves 25 each with a height control plate 26 therein, two walls of the height adjusting grooves 25 are respectively provided thereon with an upper recess 251 and a lower recess 252, and the height control plates 26 respectively have a positioning protrusion 261 in cooperation engagement with the upper and the lower recesses 251, 252; the two height control plate 26 has on its bottom two protruding pieces 262 respectively provided to enclose the top and the bottom of a rear carrier sheet 32, and the positioning trough 23 further is provided in front of it and on its top with two pressing cams 27 in contact with an upper edge of the rear carrier sheet 32.

Figure 6:
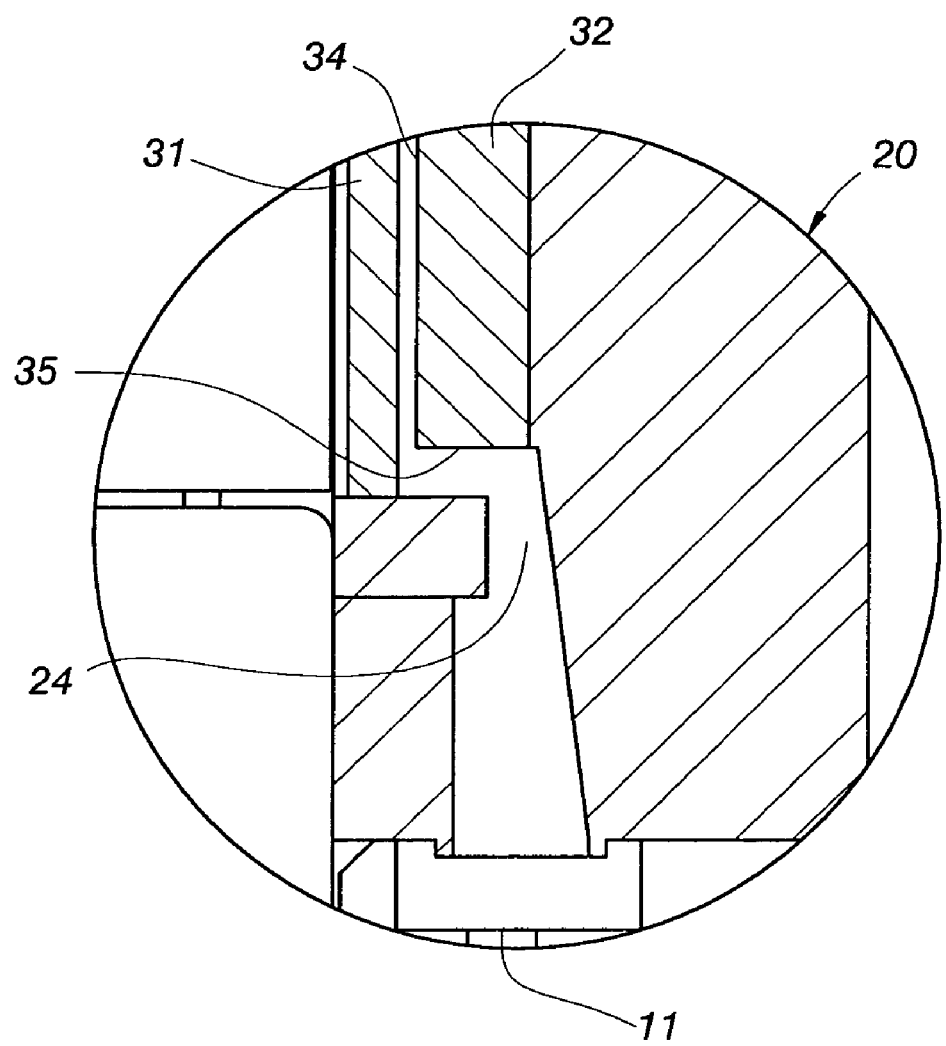
FIG. 6 is an enlarged sectional view showing a part of FIG. 5.

Referring to FIGS. 4-6, the carrier sheet set 30 includes a front carrier sheet 31, the abovementioned rear carrier sheet 32 and two spacing sheets 33 between the front and the rear carrier sheets 31, 32, so that the two carrier sheets 31, 32 are kept a suitable space or form therebetween a thin sheet receiving space 34 of which the bottom is provided with an elongate narrow seam 35, the width of the gel output port 11 is in coincident with that of the narrow seam 35 and is located below the latter.

As shown in FIGS. 4-8, with the above combination, the present invention can be used to produce gradient gel, in the method of production, two wriggling pumps 16 are used to control supply of the two liquid basic materials, wherein the first kind of the liquid basic materials is continuously input to the collecting trough 12 with a predetermined amount, and then the second kind liquid basic material is input to the collecting trough 12, by continuously rotating of the roller 13, the two liquid basic materials input to the collecting trough 12 are output directly, thus the second kind liquid basic material enters the first kind liquid basic material in a mode of gradually increasing mixing ratio, thereby the continuously output liquid gel can form a gradient by the fact that the mixing ratio of the second kind liquid basic material is gradually increased.

When the liquid gel passes continuously from the gel output port 11 facing upwards to be injected into the narrow seam 35 via the elongate hole 24, the liquid gel will be pushed gradually and upwardly from below with its surface kept horizontal, and enters the thin sheet receiving space 34 from its bottom of the carrier sheet set 30.

Figure 8:
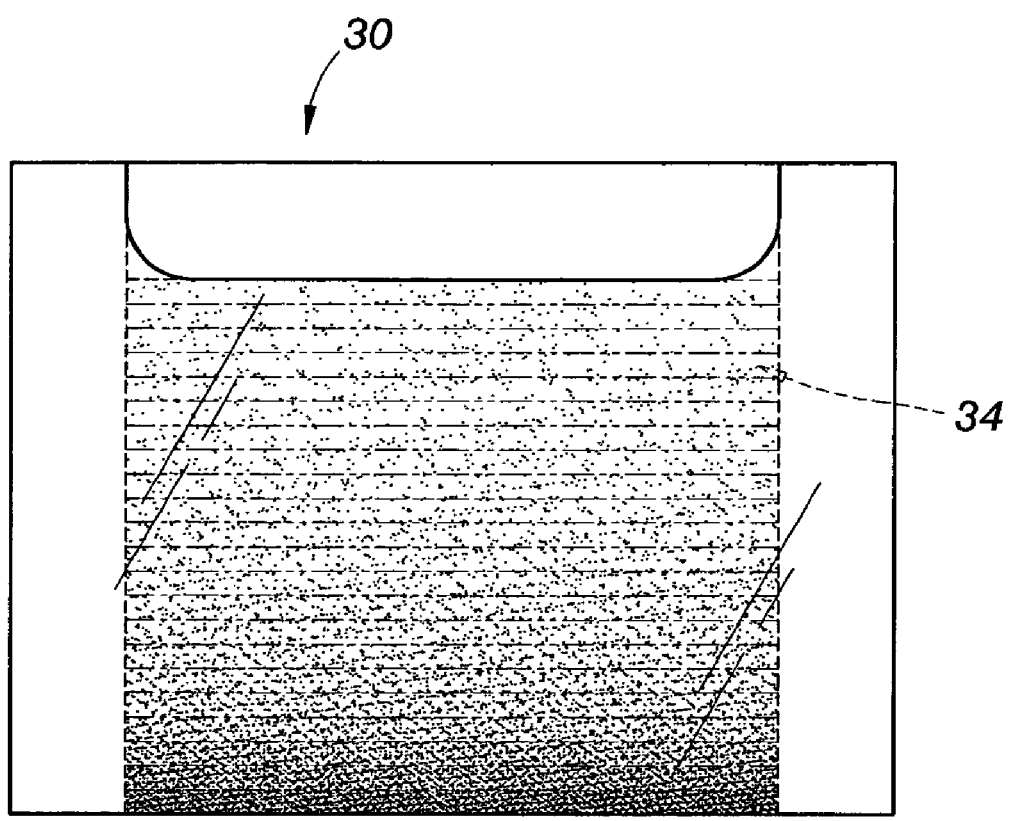
FIG. 8 is a schematic view showing injection of liquid gel in the most preferred embodiment of the device of the present invention.

As shown in FIG. 8, when the liquid gel is injected continuously to the thin sheet receiving space 34 of the carrier sheet set 30, the former injected liquid gel can be pushed upwards by the latter injected liquid gel and is gradually injected into the thin sheet receiving space 34, in cooperation with the gradually increasing density of the liquid gel, the gel is formed with a gradient of which the density is gradually increased downwardly from above.

Figure 9:
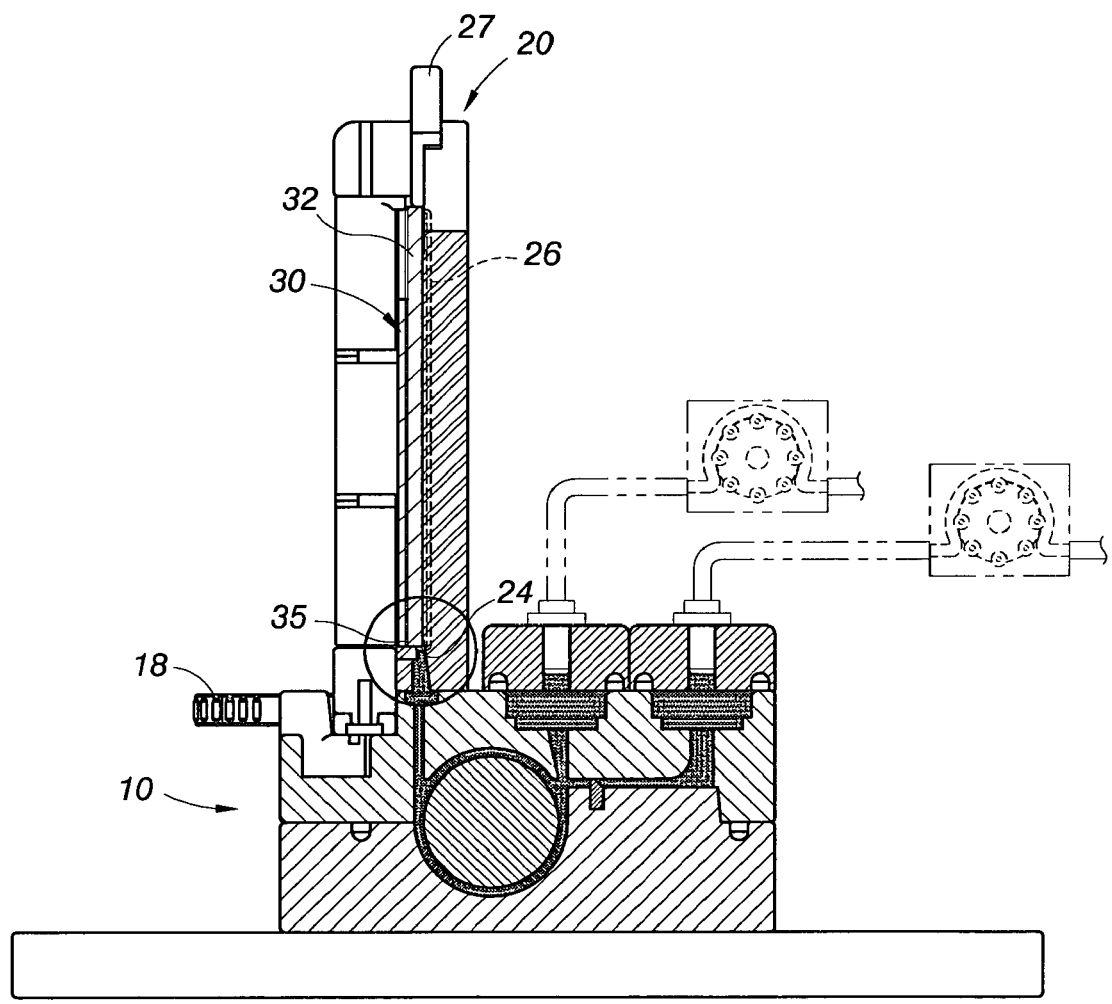
FIG. 9 is a sectional view showing sealing of a narrow seam in the most preferred embodiment of the device of the present invention.
Figure 10:
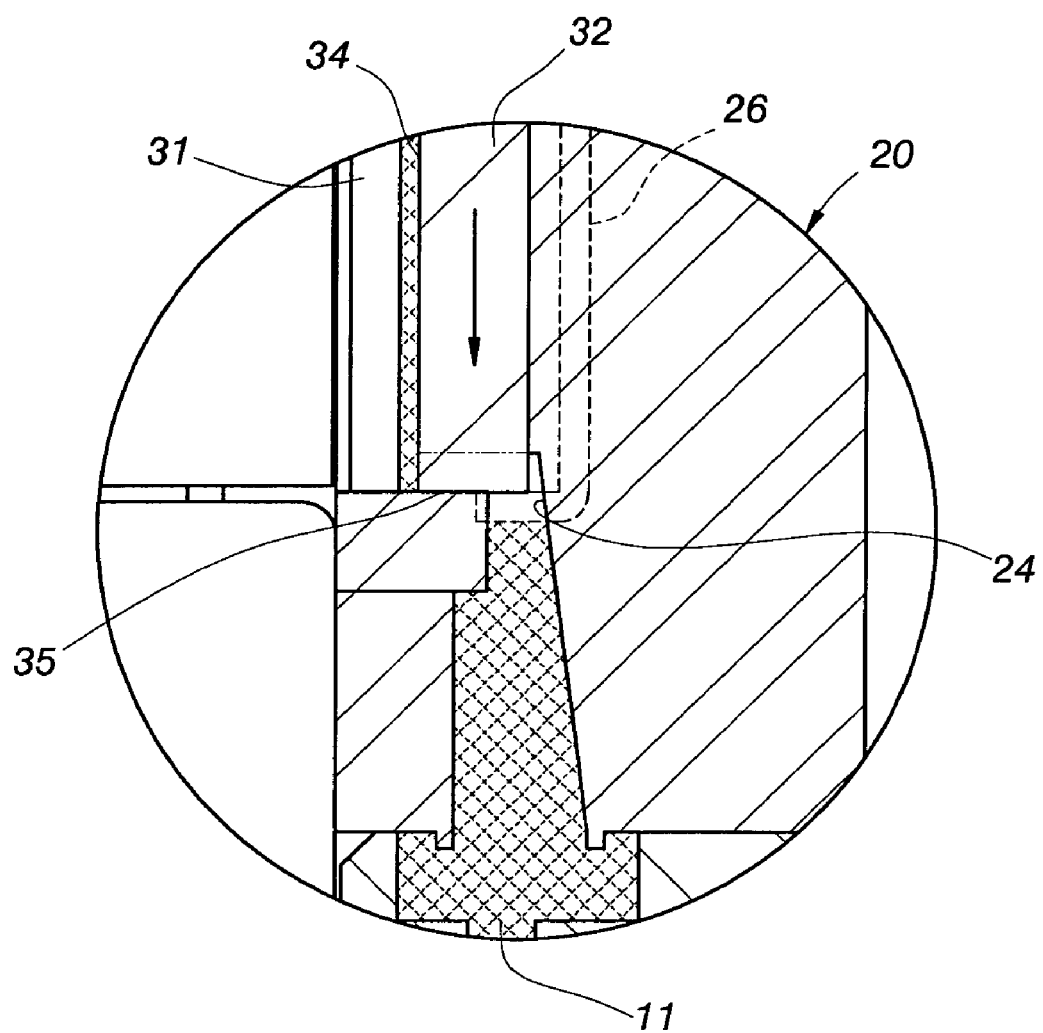
FIG. 10 is an enlarged sectional view showing a part of FIG. 9.

After injection of the liquid gel, the pressing cams 27 can be pressed down as are shown in FIGS. 9 and 10 to lower the rear carrier sheet 32 and the height control plate 26, the bottom of the rear carrier sheet 32 abuts on and seal the elongate hole 24 and the narrow seam 35. At this time, so long the liquid gel is cured, the two positioning handles 18 of the seat 10 is rotated to relieve the positioning of the positioning member 20, and the carrier sheet set 30 injected with the liquid gel is dismantled together with the positioning member 20, and then an accomplished gel product can be obtained.

By the fact that the gradient liquid gel of the present invention is pushed gradually and upwardly from below, this may render the liquid gel in an identical level to have same density and mixing ratio. Thus gradient gel being more accurate and more stable in quality can be produced, and there will no bubble generated in the process of production.

The embodiments given and shown in the drawings are only for illustrating the present invention, and not for giving any limitation to the scope of the present invention; it will be apparent to those skilled in this art that various equivalent modifications or changes without departing from the spirit of this invention shall also fall within the scope of the appended claims.

The invention claimed is:

1. A method of gradient gel electrophoresis shaping, comprising:

Causing a first kind of at least two liquid basic materials to be continuously input into a collecting trough of a seat, wherein a roller is at least partially disposed within the collecting trough, the liquid basic materials suitable for generating a gradient gel;

Causing a second kind of said basic liquid materials to be input into said collecting trough;

Causing a mixing ratio of said second kind of liquid basic materials to said first kind of liquid basic materials to increase as the liquid basic materials are input into the collecting trough;

Causing said roller to rotate; and

Outputting said liquid basic materials from said collecting trough into a receiving space within a carrier sheet set that is held in static relationship with said seat, thereby continuously outputting liquid gel into said statically held carrier sheet set that forms a gradient by virtue of said increasing mixing ratio, wherein said carrier sheet set includes a front carrier sheet, a rear carrier sheet and at least two spacing sheets between said front and said rear carrier sheets, so that said front and rear carrier sheets form therebetween said receiving space; and Said positioning member includes a positioning frame fixed on said seat, two lateral pressing plates pivotally provided at two lateral sides of and in front of said positioning frame, A front of said positioning frame is provided with a positioning trough for accepting said carrier sheet set, a bottom of said positioning trough provided with an elongate hole in fluidic connection with said gel output port;

Lateral sides of a front wall of the positioning trough each including an upright height adjusting groove with a height control plate disposed therein, each height adjusting groove including an upper and lower recess, and each height control plate has a positioning protrusion configured to selectively engage with the corresponding upper and lower recesses;

Each height control plate has thereon at least two protruding pieces respectively provided on a top and a bottom end thereof configured to engage with said rear carrier sheet; and A top of a front of said positioning trough further including at least two pressing camps in contact with an upper edge of said rear carrier sheet.

2. A gel electrophoresis shaping device at least comprising:

A seat having an elongate gel output port with an opening facing upwards, said seat being provided at an upstream end of said gel output port with a collecting trough which is provided therein with a roller, and said collecting trough is provided at an upstream thereof with at least two receiving troughs for receiving different liquid basic materials, each of the at least two receiving troughs being provided with a flow channel in fluid communication with said collecting trough, A positioning member provided on an upper periphery of said gel output port, said positioning member configured to accept and statically mount a carrier sheet set vertically on said positioning member, said carrier sheet set having sheet receiving space of which a bottom therefor is provided with an elongated seam, at least a portion of said get output port coincident with said elongated seam and located below said elongated seam so that gel output from said gel output port is input into said sheet receiving space through said seam, Wherein said carrier sheet set includes a front carrier sheet, a rear carrier sheet and at least two spacing sheets between said front and said rear carrier sheets, so that said front and rear carrier sheets form therebetween said sheet receiving space; and Said positioning member includes a positioning frame fixed on said seat, two lateral pressing plates pivotally provided at two lateral sides of and in front of said positioning frame;

A front of said positioning frame is provided with a positioning trough for accepting said carrier sheet set, a bottom of said positioning trough provided with an elongated hole in fluidic connection with said gel output port;

Lateral sides of a front wall of the positioning trough each including an upright height adjusting groove with a height control plate disposed therein, each height adjusting groove including an upper and a lower recess, and each height control plate has a positioning protrusion configured to selectively engage with the corresponding upper and lower recesses;

Each height control plate has thereon at least two protruding pieces respectively provided on a top and a bottom thereof configured to engage with said rear carrier sheet; and A top and a front of said positioning trough further including at least two pressing cams in contact with an upper edge of said rear carrier sheet.

3. The gel electrophoresis shaping device as claimed in claim 2, wherein each of said receiving troughs is connected at an upstream side thereof with a corresponding pump to control supply of said liquid basic materials.

4. The gel electrophoresis shaping device as claimed in claim 2, wherein at least one of said flow channels is provided therein with a check valve.

5. The gel electrophoresis shaping device as claimed in claim 2, wherein a periphery of said gel output port of said seat includes a connecting groove for longitudinally placement therein of said positioning member, and lateral sides of said positioning member each includes a respective transverse positioning groove, and lateral sides of said seat each includes a respective positioning handle, each of said positioning handles including an engaging plate that is pivoted transversely to enter a corresponding one of said transverse positioning grooves.

6. The gel electrophoresis shaping device as claimed in claim 2, wherein a width of said collecting trough corresponds to a width of said gel output port, and a width of said elongate flow leading channel of each of said receiving troughs corresponds to the width of said collecting trough.

* * * * *